United States Patent [19]

Patel

[11] 4,215,699
[45] Aug. 5, 1980

[54] POSITION INDICATING DEVICE
[75] Inventor: Bhupendra C. Patel, Elgin, Ill.
[73] Assignee: The Kendall Company, Boston, Mass.
[21] Appl. No.: 892,562
[22] Filed: Apr. 3, 1978

Related U.S. Application Data

[63] Continuation of Ser. No. 680,955, Apr. 28, 1976, abandoned.

[51] Int. Cl.³ .............................................. A61B 5/00
[52] U.S. Cl. ................................... 128/748; 128/774; 128/347; 116/270
[58] Field of Search ............... 128/221, 215, 347, 673, 128/679, 748, 349 B, 218 NV; 116/270; 73/146.8

[56] References Cited

U.S. PATENT DOCUMENTS

| | | |
|---|---|---|
| 2,837,093 | 6/1958 | Tash .......................... 128/DIG. 5 X |
| 3,241,514 | 3/1966 | Grimland ...................... 116/114 PV |
| 3,452,708 | 7/1969 | Richardson ...................... 73/146.8 X |
| 3,675,722 | 7/1972 | Balmes ...................... 116/114 PV X |
| 3,731,691 | 5/1973 | Chen ............................. 128/349 B X |
| 3,736,899 | 6/1973 | Manske ......................... 116/114 PV |
| 3,780,693 | 12/1973 | Parr .............................. 116/114 PV |
| 4,000,741 | 1/1977 | Binard et al. .................. 128/218 NV |

Primary Examiner—Kyle L. Howell
Attorney, Agent, or Firm—Powell L. Sprunger

[57] ABSTRACT

A device for indicating the position of a needle in a patient's body comprising, a body member having a flexible film secured to the body member and overlying a surface of the body member, and a passageway communicating with a space between the surface and film. The body member is attached to an outer portion of the needle with the passageway communicating with the needle to indicate pressure by the film.

6 Claims, 12 Drawing Figures

POSITION INDICATING DEVICE

This is a continuation, of application Ser. No. 680,955 filed Apr. 28, 1976, now abandoned.

BACKGROUND OF THE INVENTION

The present invention relates to position testing devices for a patient's body.

During certain medical procedures, such as an epidural anesthesia procedure, it is necessary to position the tip of a needle at a relatively precise position inside the patient's body. During this particular procedure, the needle tip should be located in the potential epidural space where the body pressure is normally slightly negative, and never positive. If the needle tip has been advanced too far into the body, it projects through the dura mater into the subarachnoid space where the body pressure is positive.

Epidural anesthesia has become popular among anesthesiologists and surgeons since it does not entail the risks associated with general anesthesia, and does not require that the dura mater be punctured. However, locating the epidural space can be relatively difficult since it is a potential space, i.e., an interface between two tissues which are normally held together by a slight negative pressure. Prior testing methods for the epidural space involve the use of tactile sense with syringes or a drop of liquid placed in the needle hub. The syringe tests have not been satisfactory since they rely on subjective judgment of the user under his control. The hub or Guiteras test also has not been suitable since the liquid drop frequently falls out of the hub, and they may result in a false indication of the needle location.

SUMMARY OF THE INVENTION

A principal feature of the present invention is the provision of a device for indicating the position of a needle in a patient's body in a sure and simplified manner.

The device of the present invention comprises a hollow needle having a lumen, a tip at a distal end of the needle, and a hub at a proximal end of the needle. The device also has a body member having a cavity of an outer surface of the body member, raised indicating means in the cavity, a passageway communicating with the cavity, and a tubular section at a distal end of the body member defining an end portion of the passageway, with the tubular section being received in the needle hub with the passageway communicating with the needle lumen. The device also has a flexible film secured to the body member over the indicating means and closing the cavity. The film is normally spaced from the indicating means.

A feature of the present invention is that the film flexes against the indicating means when the needle tip communicates with a negative pressure in the patient's body.

Another feature of the invention is that in an embodiment the indicating means impresses a pattern on the film when the film contacts the indicating means.

Yet another feature of the invention is that in an embodiment the film is at least partially transparent and an indicating surface of the indicating means becomes more visible when the film contacts the indicating surface.

Still another feature of the invention is that the film flexes away from the indicating means when the needle tip communicates with a positive pressure in the patient's body.

Thus, a feature of the present invention is that the device indicates whether the needle tip communicates with a positive or negative pressure inside the patient's body.

Yet another feature of the invention is that the body member has a pair of opposed wings adjacent the proximal end of the member to facilitate placement of the needle tip in the patient's body during testing.

Still another feature of the invention is that the body member may be readily attached and removed from the needle hub.

Thus, a feature of the invention is that the testing device permits sure and simplified determination of the needle location in the patient's body.

Further features will become more fully apparent in the following description of the embodiments of this invention and from the appended claims.

DESCRIPTION OF THE PREFERRED EMBODIMENTS

Figure 1:
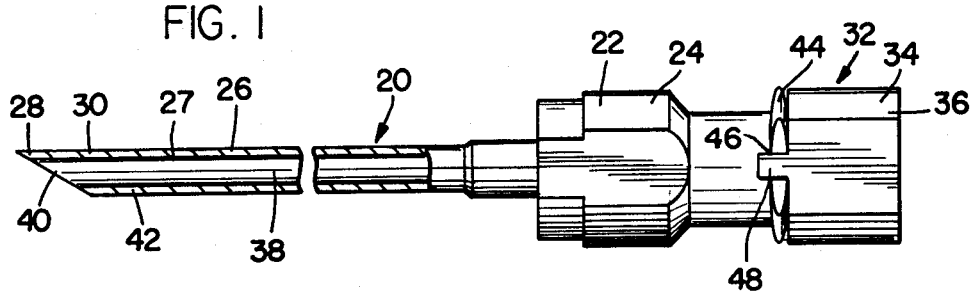
FIG. 1 is a fragmentary elevational view, taken partly in section, of a spinal needle and stylet.
Figure 2:
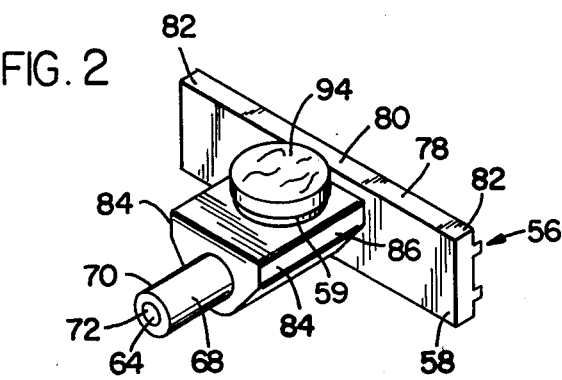
FIG. 2 is a perspective view of a position testing device of the present invention.
Figure 3:
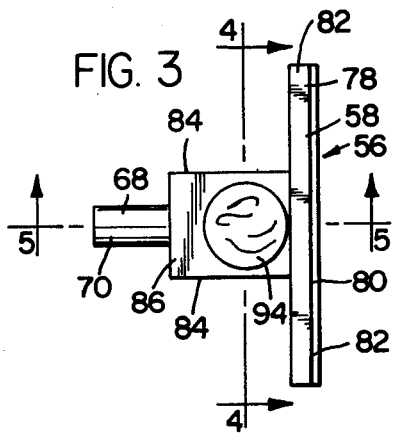
FIG. 3 is a top plan view of the testing device of FIG. 2.

Referring now to FIG. 1, there is shown a hollow spinal needle generally designated 20 having a hub 22 adjacent a proximal end 24 of the needle, a hollow shaft 26 secured to the hub 22, a lumen 27, and a bevel tip 28 adjacent a distal end 30 of the needle 20. As shown, a stylet generally designated 32 is removably received in the needle 20. The stylet 32 has an end member 34 adjacent a proximal end 36 of the stylet 32, a solid shaft 38 connected to the member 34 and received in the hollow shaft 26 of the needle 20, with the shaft 38 having a bevel tip 40 adjacent a distal end 42 of the stylet 32 forming a continuous distal end surface between the needle tip 28 and stylet tip 40 when the stylet 32 is properly positioned within the needle 20. The needle hub 22 has an outwardly directed flange 44 at its proximal end, and the flange 44 has a reference notch 46 to receive a reference protuberance 48 extending distally of the stylet member 34. Accordingly, the stylet 32 may be rotated within the needle 20 until the protuberance 48 is located in the notch 46, as shown, such that the flange 44 and member 34 mate together and position the stylet tip 40 at its proper location relative the needle tip 28.

Figure 8:
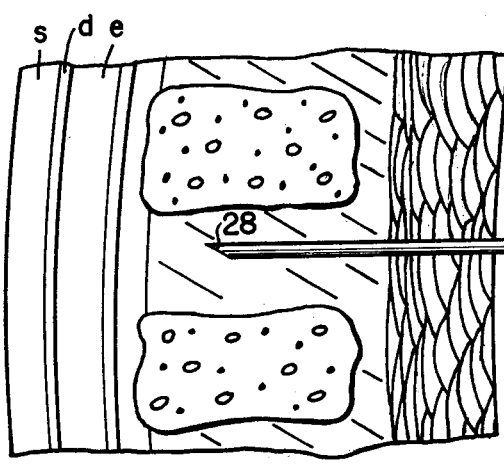
FIG. 8 is a diagrammatic sectional view of a patient's body showing the needle and stylet of FIG. 1 as positioned in the patient.

With reference to FIG. 8, at the start of an epidural anesthesia procedure, a patient may be positioned on his side and the needle 20 and internal stylet 32 are inserted by the physician into the patient's back until needle and stylet tips are located somewhat near the epidural space e of the patient. During this time, the stylet 32 prevents coring of body tissue by the needle 20. After the needle 20 has been properly positioned in the patient, the stylet 32 is removed from the needle, as will be described below.

With reference to FIGS. 2–5, there is shown a testing device generally designated 56 having a body member 58. The body member 58 has an annular extension 59 defining a cavity 60 at an outer surface 62 of the extension 59. The body member 58 has a passageway 64 communicating with a lower end of the cavity 60 at an opening 66. The body member 58 also has a tubular section 68 at a distal end 70 of the body member 58, with the tubular section 68 defining an outer end portion of the passageway 64 and an opening 72 at the distal end of the body member. As shown, the passageway 64 has a first channel 74 communicating with the cavity opening 66 and disposed generally vertically when the cavity 60 is placed in an upright position, and a second channel 76 disposed generally horizontally during testing and communicating between the channel 74 and the end opening 72. The body member 58 also has an elongated bar 78 at a proximal end 80 of the body member 58 defining a pair of opposed wings 82 which extend past opposed sides 84 of the body member 58. As shown, a central portion 86 of the body member 58 connects the tubular section 68 and the elongated bar 78. The body member 58 may be made of any suitable material, such as plastic.

Figure 4:
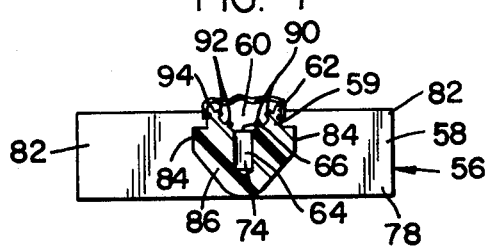
FIG. 4 is a sectional view taken substantially as indicated along the line 4—4 of FIG. 3.
Figure 5:
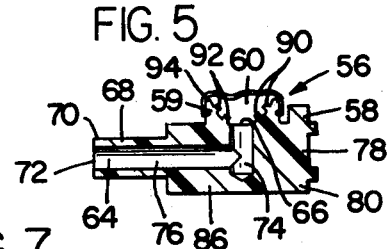
FIG. 5 is a sectional view taken substantially as indicated along the line 5—5 of FIG. 3.
Figure 7:
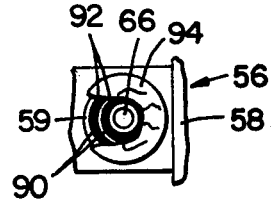
FIG. 7 is a fragmentary plan view, partly broken away, showing an embodiment of an indicating surface for the device of FIG. 2.

With reference to FIGS. 4, 5, and 7, the body member 58 has a plurality of raised members 90 defining relatively flat indicating surfaces 92 which are recessed in the cavity 60. In the embodiment shown, the raised members 90 comprise a pair of concentric rings, with the opening 66 communicating with the cavity inside the smaller inner ring. With reference to FIG. 7, the indicating surfaces 92 may have a color contrast, such as red or black, for a purpose which will be described below.

Figure 6:
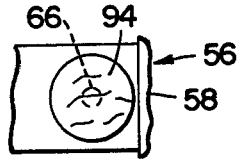
FIG. 6 is a fragmentary plan view showing a film of the device prior to contact with an indicating surface.
Figure 11:
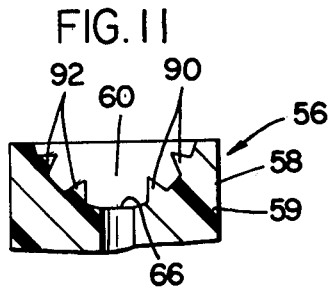
FIG. 11 is a fragmentary sectional view of another embodiment of the device of the present invention.

With reference to FIGS. 2–7, the device 56 also has a flexible film 94 secured to the extension 59 over the raised members 90 and closing the cavity 60. As shown in FIGS. 4 and 5, the indicating surfaces 92 face the film 94, and the film 94 is normally spaced from the surfaces 92. In one embodiment, the film 94 may be made of a transparent or translucent material, such as polyethylene, and in another embodiment may be made of an opaque material, such as rubber. If the film 94 is translucent or transparent, the indicating surfaces 92 of the raised members 90 are barely visible, if at all, when the film 94 is spaced from the surfaces 92, as shown in FIG. 6. However, when the film 94 contacts the indicating surfaces 92, the surfaces 92 become readily visible through the film 94. Visibility of the surfaces 92 through the film 94 is enhanced by the color contrast on the surfaces 92, as previously described in connection with FIG. 7. Alternatively, if the film 94 is opaque, the pattern of the raised members 90 is impressed on the film when the film 94 is drawn against the raised members 90. In this case, with reference to FIG. 11, impression of the pattern by the raised members 90 is enhanced by the tapered members 90 defining lines for the indicating surfaces 92 facing the film.

Figure 9:
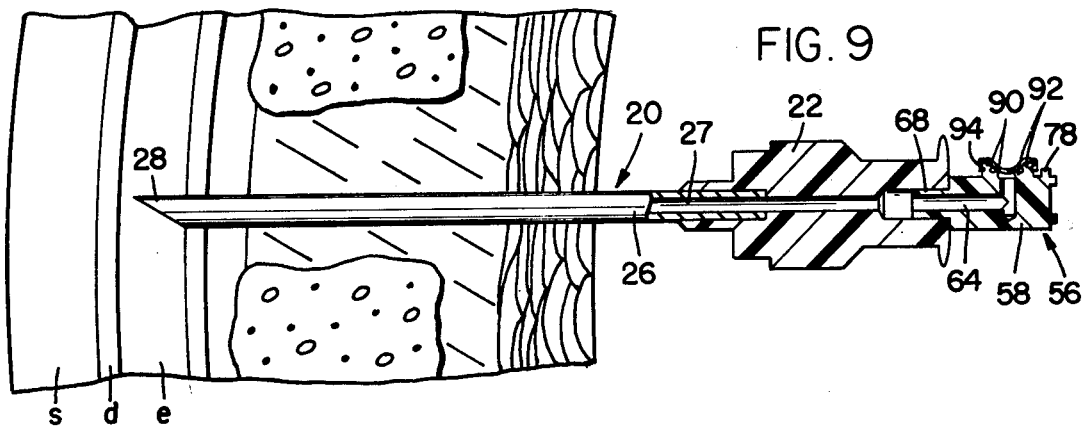
FIG. 9 is a diagrammatic sectional view of the patient's body showing the needle tip as positioned in the epidural space of the patient.
Figure 10:
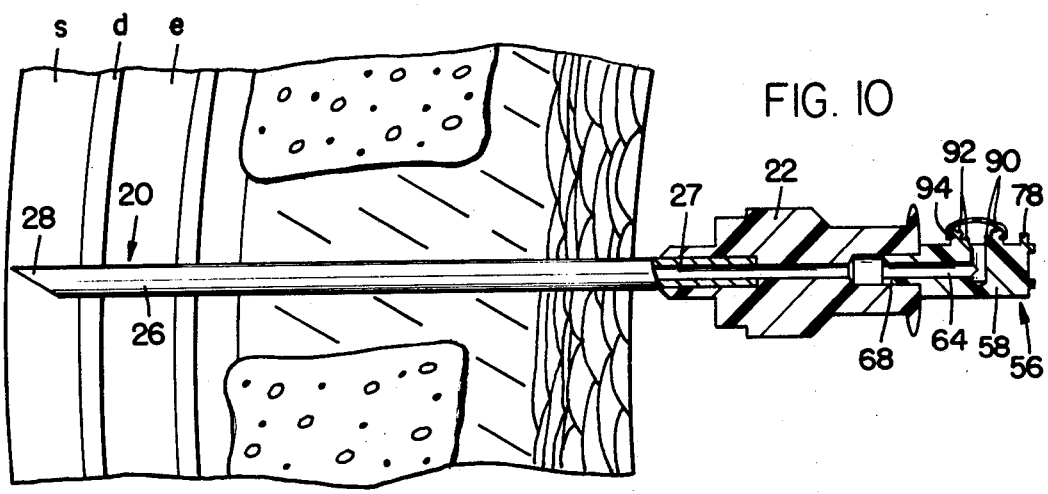
FIG. 10 is a diagrammatic sectional view of the patient's body showing the needle tip as positioned in the subarachnoid space of the patient.

The use of the device 56 for testing the needle location in a patient's body is described as follows. With reference to FIGS. 8–10, after the needle 20 and stylet 32 have been positioned in the body, as previously described, the stylet 32 is removed from the needle 20. Next, the testing device is attached to the needle hub 22 by positioning the tubular section 68 of the body member 58 in the lumen 27 of the hub 22, and with the film 94 the device 56 located in an upright position to permit clear vision of the film. Referring to FIG. 9, the physician grasps the opposed wings of the bar 78, and advances the needle 20 and the attached body member 58 slightly into the patient's body. When the needle tip is located in the epidural space e of the patient, the needle tip communicates with a slight negative pressure in the epidural space e, causing the film 94 to be drawn against the indicating surfaces 92 of the raised members 90. In the case of a translucent or transparent film, the indicating surfaces 92 will become readily visible through the film 94, while in the case of an opaque film, a pattern will be impressed on the film 94 by the raised members 90. In both cases, visibility of the indicating surfaces or the impressed pattern indicates that the needle tip 28 is properly located in the epidural space e of the patient. However, with reference to FIG. 10, if the needle tip 28 has been inadvertently passed through the dural mater d into the subarachnoid space s, the needle 26 communicates with a positive pressure in the subarachnoid space s causing the film 94 to flex outwardly from the body member. Accordingly, the inflated film 94 also indicates whether the needle tip has improperly punctured the dura mater d, in which case the needle 20 must be withdrawn a slight distance from the patient, and the device may be again used to determine when the needle tip 28 has been located in the epidural space e. After the needle has been properly positioned in the patient with the needle tip 28 located in the epidural space e, the testing device 56 is removed from the needle hub 22, and the epidural anesthesia procedure proceeds in the normal manner.

Thus, in accordance with the present invention the testing device permits easy attachment and removal of the body member 58 from the needle hub 22, and provides a sure indication when the needle tip has been properly positioned in the epidural space e of the patient. The testing device 56 also indicates whether the needle tip 28 has been improperly positioned in the subarachnoid space s of the patient. Alternatively, during certain procedures it is necessary to position the needle tip in the subarachnoid space, and the device of the present invention may be used to indicate when the needle tip has punctured the dura mater and is properly located in the body.

Figure 12:
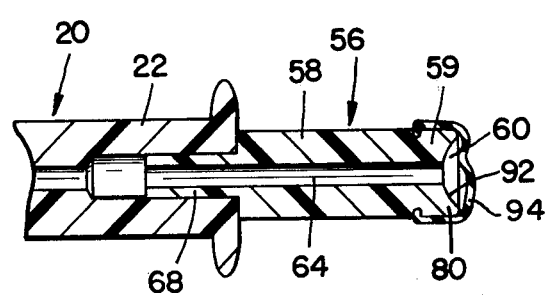
FIG. 12 is a sectional view of another embodiment of the testing device of the present invention.

Another embodiment of the present invention is illustrated in FIG. 12, in which like reference numerals designate like parts. In this embodiment, the annular extension 59 defining the cavity 60 is located at the proximal end 80 of the body member 58. The film 94 is secured over the cavity 60 in a manner as previously described. However, in this embodiment, the body member 58 defines a continuous indicating surface 92 which underlies the film 94, and the film 94 is preferably translucent or transparent to indicate when the film 94 contacts the indicating surface 92 responsive to a negative pressure in the passageway 64.

According to a method of the present invention the position of a needle assembly in a patient's body is tested by advancing a tip of the assembly into the patient's body, and modifying the visibility of an indicating surface through a film responsive to a change of body pressure adjacent the tip. According to another method of the invention, the position of the assembly is tested by advancing a tip of the assembly into a patient's body, and by impressing a pattern on a film responsive to a negative pressure in the assembly.

The foregoing detailed description is given for clearness of understanding only, and no unnecessary limitations should be understood therefrom, as modifications will be obvious to those skilled in the art.

I claim:

1. A device for indicating the position of the tip of a needle in the epidural space within a patient's body where the body pressure is slightly negative, comprising:
   a hollow needle having a tip with an opening at a distal end of the needle for placement within said patient's body, a lumen communicating with the tip opening, and a hub at a proximal end of the needle;
   a body member having a cavity at an outer surface of the body member, raised indicating means in said cavity, a passageway communicating with the cavity, and a tubular section at a distal end of the body member defining an end portion of the passageway, said tubular section being received in the needle hub with the passageway communicating with the needle lumen and the tip opening; and
   a flexible film mounted on said body member normally spaced outwardly from and extending across said indicating means and forming an outer wall of said cavity, said film flexing inwardly into contact with said indicating means when the needle tip opening communicates with said slight negative pressure in said epidural space within said patient's body.

2. The device of claim 1 wherein said body member includes a pair of opposed wings to facilitate placement of the hollow member in the patient's body during testing.

3. The device of claim 1 wherein said indicating means comprises a plurality of concentric rings.

4. The device of claim 3 wherein the passageway means communicates with an inner part of the cavity inside an inner of said plural rings.

5. The device of claim 1 wherein said film is opaque.

6. The device of claim 1, wherein said film is at least partially transparent, and in which said indicating means becomes more clearly visible when the film contacts said indicating means.

* * * * *